(12) United States Patent
Bonnet (10) Patent No.: US 10,821,291 B2
(45) Date of Patent: Nov. 3, 2020

(54) AUTONOMOUS CARDIAC IMPLANT OF THE "LEADLESS CAPSULE" TYPE, WITH DETECTION OF ATRIAL ACTIVITY BY ANALYSIS OF THE CHARGING ELECTRIC SIGNAL DELIVERED BY AN ENERGY HARVESTING MODULE

(71) Applicant: CAIRDAC, Antony (FR)

(72) Inventor: Jean-Luc Bonnet, Massy (FR)

(73) Assignee: CAIRDAC, Antony (FR)

( * ) Notice: Subject to any disclaimer, the term of this patent is extended or adjusted under 35 U.S.C. 154(b) by 173 days.

(21) Appl. No.: 16/198,872

(22) Filed: Nov. 22, 2018

(65) Prior Publication Data

US 2019/0151666 A1 May 23, 2019

(30) Foreign Application Priority Data

Nov. 22, 2017 (FR) ..................................... 17 61034

(51) Int. Cl.
| | | |
|---|---|---|
| *A61N 1/378* | (2006.01) | |
| *A61N 1/375* | (2006.01) | |
| *A61N 1/365* | (2006.01) | |
| *A61N 1/368* | (2006.01) | |
| *A61B 5/00* | (2006.01) | |
| *H01L 41/113* | (2006.01) | |
| *H02N 2/18* | (2006.01) | |
| *A61N 1/39* | (2006.01) | |
| *A61N 1/02* | (2006.01) | |

(52) U.S. Cl.
CPC ............ *A61N 1/3785* (2013.01); *A61B 5/686* (2013.01); *A61N 1/3682* (2013.01); *A61N 1/3684* (2013.01); *A61N 1/36507* (2013.01); *A61N 1/3756* (2013.01); *A61N 1/37512* (2017.08); *A61N 1/37518* (2017.08); *H01L 41/1136* (2013.01); *H02N 2/186* (2013.01); *A61B 5/6869* (2013.01); *A61N 1/025* (2013.01); *A61N 1/3956* (2013.01)

(58) Field of Classification Search
CPC .............. A61N 1/3785; A61N 1/37512; A61N 1/37518; A61N 1/36507; A61N 1/3682; A61N 1/3684; A61N 1/3756; A61N 1/025; A61N 1/3956; A61B 5/6869; A61B 5/686; H01L 41/1136; H02N 2/186
See application file for complete search history.

(56) References Cited

U.S. PATENT DOCUMENTS

| | | |
|---|---|---|
| 2009/0171408 A1 | 7/2009 | Solem |
| 2013/0238073 A1 | 9/2013 | Makdissi et al. |
| | (Continued) | |

*Primary Examiner* — Paula J Stice
(74) *Attorney, Agent, or Firm* — Steven M. Greenberg, Esq.; Shutts & Bowen LLP (57) ABSTRACT

An energy harvester converts into electrical energy the external stresses applied to the implant at the heartbeat rhythm. This harvester includes an inertial unit and a transducer delivering an oscillating electrical signal that is rectified and regulated for powering the implant and charging an energy storage component. The instantaneous variations of this electrical signal are analyzed in a detection window following or preceding a ventricular contraction, to obtain atrial activity information representative of the atrium contribution to the electric signal, in particular information about the presence/absence of a spontaneous atrial contraction, and/or parameters making it possible to determine an atrioventricular delay to be applied if the ventricle has to be stimulated.

16 Claims, 7 Drawing Sheets

(56) References Cited

U.S. PATENT DOCUMENTS

| | | |
|---|---|---|
| 2015/0005838 A1 | 1/2015 | Renesto et al. |
| 2016/0114161 A1 | 4/2016 | Amblard et al. |
| 2017/0274213 A1 | 9/2017 | Ghosh et al. |

AUTONOMOUS CARDIAC IMPLANT OF THE "LEADLESS CAPSULE" TYPE, WITH DETECTION OF ATRIAL ACTIVITY BY ANALYSIS OF THE CHARGING ELECTRIC SIGNAL DELIVERED BY AN ENERGY HARVESTING MODULE

CROSS REFERENCE TO RELATED APPLICATIONS

This application claims priority under 35 U.S.C. § 119(a) to French Patent Application Serial Number 1761034, filed Nov. 22, 2017, the entire teachings of which are incorporated herein by reference.

BACKGROUND OF THE INVENTION

Field of the Invention

The invention relates to an active implantable medical device (AIMD), in particular cardiac implants for monitoring the myocardium activity and delivering stimulation, resynchronization or defibrillation pulses in case of rhythm disorder detected by the device, and more particularly to those devices which incorporate a self-powering system.

Description of the Related Art

An AIMD which incorporates a self-powering system includes a mechanical energy harvesting device associated with an integrated energy storage component, such as a rechargeable battery or a high-performance capacitor. The harvesting device, also called harvester or scavenger, collects the mechanical energy resulting from the various movements undergone by the body of the implanted device. Those movements may have for origin a certain number of phenomena occurring at the rhythm of the heartbeats, in particular periodic shakings of the wall on which the implant is anchored, cardiac tissue vibrations related inter alia to the closings and openings of the cardiac valves, or blood flow variations in the surrounding environment, which stress the implant and make it oscillate at the rhythm of the flow rate variations. The mechanical energy collected by the harvester is converted into electrical energy (voltage or current), by means of a suitable mechanical-electrical transducer, for powering the various circuits and sensors of the device and for charging the energy storage component.

This energy harvesting technique is particularly well adapted for powering implanted autonomous capsules having no physical connection with a remote device. These capsules are called for this reason "leadless" capsules, for distinguishing them from the electrodes or sensors arranged at the distal end of a lead, through the whole length of which run one or several conductors connected to a generator connected to the opposite, proximal end.

In the cardiac application case, they may be epicardic leadless capsules, attached to the outer wall of the heart, or endocavitary capsules, attached to the inner wall of a ventricular or atrial cavity, or capsules attached to a wall of a vessel near the myocardium. The invention is nevertheless not limited to a particular type of capsule, and it is as well applicable to any type of leadless capsule, whatever the operational purpose thereof.

The attachment of the capsule to the implantation site is made using a protruding anchoring system extending the capsule body and intended to enter the cardiac tissue, in particular by means of a screw. The capsule moreover includes various electronic circuits, sensors, etc., as well as wireless communication emitter/receiver means for the remote exchange of data, all of them being integrated in a body of very small size that can be implanted into sites whose access is difficult or that leave little room, such as the ventricle apex, the inner wall of the atrium, etc. United States Patent Application Publication 2009/0171408 A1 (Solem) describes various examples of such leadless intracardiac capsules.

In any case, the processing of the signals within the capsule and the remote transmission thereof requires a non-negligible energy with respect to the energetic resources that this capsule can store into a very small available volume. Now, taking into account its autonomous character, the capsule can only use its own resources, hence the necessity of an integrated self-powering system including an energy harvester combined to a small integrated energy storage component.

There exist several types of energy harvesters, based on different physical principles: system of the automatic wind-up watch movement type, mobile magnet system, bellows system or the like for collecting the blood pressure variations, etc.

The invention more particularly relates to leadless capsules (or similar implantable devices) whose energy harvester uses an inertial unit subjected to the above-described external solicitations. This inertial unit may in particular implement—but without limitation—a transducer coupled to a pendular mechanism including in the capsule a mobile mass, called "seismic mass" or "inertial mass". This inertial mass is driven according to the movements of the capsule, which is permanently subjected to the various external stresses described hereinabove. After each of these stresses, the inertial mass, which is coupled to an elastically deformable element, oscillates at a natural frequency of free oscillation.

Other types of inertial units for an energy harvester also show this oscillation phenomenon. In any case, the invention is not limited to a particular type of inertial unit, and covers not only the units with an electromechanical transducer but also those with a piezoelectric, electromagnetic, electrostatic or tribological transducer, all adapted to deliver an electrical signal under the effect of an external mechanical stress.

The oscillation frequency of the inertial unit, typically of the order of a few tens of hertz, is in particular higher than the frequency of the external cyclic stresses that correspond to the heartbeat rate (at most a few hertz). Hence, at each cardiac contraction, the seismic mass (or another functionally similar mechanical component) will be stressed with a higher or lower amplitude, then the inertial system will oscillate several times with decreasing amplitudes (bounces characteristic of a damped periodic oscillation), and will finally stabilize up to the following heartbeat, where the stress/oscillations cycle will occur again in a comparable manner.

The mechanical energy of the inertial unit oscillation is for example converted into an electrical energy by a mechanical-electrical transducer producing an electrical signal. This signal is delivered to a power management circuit of the implant, which rectifies and regulates the electrical signal to deliver as an output a stabilized direct voltage or current, for powering the various electronic circuits and sensors of the implant, as well as for charging the energy storage component.

Advantageously, but without limitation, the mechanical-electrical transducer may be a piezoelectric component cyclically and alternately stressed in flexion so as to generate within the material that constitutes it electrical charges that are collected at the surface of the component to be used by the self-powering system of the capsule.

The piezoelectric component may for example be a piezo-electric beam fitted at one end and coupled to the inertial mass at the other end, which is free. Reference can be made in particular to European Patent Application Publication EP 2 857 064 A1 (Sorin CRM), which describes such an energy harvester arrangement, particularly suitable for powering a leadless capsule.

The so-harvested and stored electrical energy is used to power the different circuit of the leadless capsule.

The implantation of a leadless capsule into a ventricle makes it possible to obtain very easily a "single chamber" stimulator configuration (stimulation of a single cavity, generally the right ventricle). For that purpose, the leadless capsule is provided with a detection/stimulation electrode in contact with the ventricle wall, which allows it to detect the presence or not of a spontaneous ventricular depolarization wave, as well as the instant of occurrence of this wave (ventricular marker). If necessary, in the event of absent or late spontaneous depolarization, this electrode also allows delivering a stimulation pulse to the ventricle so as to trigger the contraction thereof.

This mode of operation is called VVI (i.e. with ventricular detection and stimulation, and inhibition of the stimulation upon detection of a ventricular signal out of the refractory period). It is limited to a stimulation for which an escape interval (EI) is programmed so as either to cause the stimulation if the duration elapsed since the last detection or stimulation of the ventricle exceeds the duration of this escape interval, or to do nothing if a spontaneous ventricular depolarization is detected.

It hence suffers from the drawback that the ventricular stimulation is not synchronous with the atrium contraction, so that the stimulation rate does not adapt to the sinus rhythm at a given instant (sinoatrial rhythm).

The detection of the atrial activity, with determination of the instant when the atrium contracts, would allow determining the patient's instantaneous sinus rhythm and hence calculating and applying an atrioventricular delay (AVD) depending on this rhythm. This stimulation mode, called VDD (ventricular stimulation, double atrial and ventricular detection, and stimulation depending on the atrial and ventricular events detected) is not conceivable with a simple ventricular leadless capsule, which, by definition, has no lead and includes no element in the remote atrium region that would allow a direct detection of the sinus rhythm.

The above-mentioned United States Patent Application Publication 2009/0171408 A1 of course provides for the possibility to derive from the electrical signal produced by the harvester information representative of the heart kinetic energy, or of the degree of acceleration of the rhythm, i.e. a general indication of the myocardium level of activity, in particular for diagnosing a state of cardiac insufficiency. But this mechanism provides no specific information about the atrium activity, which would make it possible in particular to determine whether or not the latter contracts, at which rate and at what time.

The problem is, in such a case, to be able to detect an atrial activity based on the single leadless capsule implanted in the ventricle, with no means nor possibility to directly collect, using an atrial lead, a signal reflecting an electrical activity of the atrium.

United States Patent Application Publication 2016/0114161 A1 proposes a solution consisting in providing the leadless capsule with an endocardiac acceleration sensor (EA sensor) incorporated in the capsule, which makes it possible to observe in the EA signal delivered by this sensor a so-called "EA4" or "EA0" component, whose presence or absence reveals the existence or not of a contraction of the atriums, and to estimate the instant of occurrence of this contraction.

Other solutions have been proposed, consisting for example in providing the capsule with an extension in the form of an antenna wire extending up to the right atrium and coming into contact with the atrium wall to perform detections//stimulations thereon (United States Patent Application Publication 2013/0325081 A1). Another solution consists in detecting far-field electrogram signals using an additional electrode located on a region of the leadless capsule that is not in contact with the ventricle wall. The detection of the atrial activity is based on a comparison between near field and far field, wherein an atrial activity is supposed to be detected when the far-field signal exceeds a threshold and the near-field signal does not exceed it (United States Patent Application Publication 2013/0138006 A1).

However, all these solutions remain complex to implement and, in practice, their reliability is often insufficient to detect the presence or not of an atrial activity with a high degree of certainty, and an accurate determination of the instant of occurrence of the atrial contraction. The detection of an electrical activity indeed particularly suffers from various disturbances, artefacts and interferences.

Moreover, the solutions based on the detection of the atrium mechanical activity (such as those based on the analysis of the endocardiac acceleration) are all affected, on the hemodynamic plane, by the so-called "electro-mechanical" delay between the instant when an electrical stimulation is delivered to the ventricle (electrical event) and the atrium contraction itself (hemodynamic event). Actually, the atrio-ventricular delay applied by the device, called "mechanical-electrical delay", is sub-optimum, whereas the calculation of a "mechanical-mechanical" delay based only on the hemodynamics would correspond to the physiological reality of the contraction of the cardiac cavities, independently from the electrical activity thereof.

BRIEF SUMMARY OF THE INVENTION

The object of the invention is to solve these different problems by proposing a means for detecting an atrial activity, adapted to be implemented by a leadless capsule without adding sensors, accessories or circuits liable to increase the device complexity; which provides, with a high degree of reliability, information about the presence/absence of an atrial contraction; which, in presence of a detected atrial contraction, delivers a marker indicating reliably and accurately the instant of occurrence of this contraction; that, in a manner reflecting faithfully the physiological phenomenon of mechanical contraction of the atrium, without introducing a bias related to a electro-mechanical delay.

The basic idea of the invention consists in analyzing the variations in the very short term of the electrical signal delivered by the energy harvester, between two heartbeats. This analysis is operated in real time on the signal reflecting the inertial unit oscillations (typically, the inertial mass oscillations in the case of a pendular unit) at its oscillation frequency just after the cardiac contraction. Advantageously, and characteristically of the invention, the information making it possible to prove the presence of an atrial contraction and to characterize the instant of occurrence thereof are derived from the only electrical signal produced by the energy harvester, without having to provide the implant with one or several specific sensors—the inertial unit (typically, the inertial mass/mechanical-electrical transducer pendular unit) then playing a double role of energy harvester and atrial contraction detector.

For that purpose, the invention proposes an autonomous cardiac implant of the leadless capsule type including, in manner known per se, an implant body provided with means for anchoring to a cardiac wall, the implant body accommodating an electronic unit and an energy harvesting module with an energy storage component for powering the electronic unit.

The energy harvesting module is adapted to convert into electrical energy external stresses applied to the implant body under the effect of movements of a wall to which the implant is anchored and/or of blood flow rate variations in the environment surrounding the implant at the heartbeat rhythm and/or of cardiac tissue vibrations.

The energy harvesting module includes: an inertial unit subjected to the external stresses; a transducer adapted to convert the mechanical energy produced by the oscillations of the inertial unit into an oscillating electrical signal; and a power management circuit, adapted to rectify and regulate the oscillating electrical signal, to deliver as an output a stabilized direct voltage or current, for powering the electronic unit and/or charging the energy storage component.

Characteristically of the invention, the implant further includes atrial detection means, adapted to analyze, between successive beats, the oscillating electrical signal to derive therefrom atrial activity information likely to prove in the heartbeats the presence of an atrial event and/or to characterize the instant of occurrence thereof.

According to various advantageous subsidiary characteristics, the atrial activity information is information about the presence/absence of an atrial contraction; and, the implant further includes ventricular detection means, adapted to deliver a ventricular time marker defining an instant of occurrence of a ventricular event of a cardiac beat, and means for defining a detection window, preceding or following the ventricular time marker, the atrial detection means being means adapted to analyze the variations of the oscillating electrical signal by searching for an atrial activity component within the detection window.

In this latter case, the ventricular detection means may be means adapted to derive the ventricular time marker by analyzing the variations of the oscillating electrical signal delivered by the transducer. Very preferably, the implant further includes:
- ventricular detection means, adapted to detect the occurrence, or the absence of occurrence, of a spontaneous ventricular event in a heartbeat;
- ventricular stimulation means, adapted to apply a ventricular stimulation in the absence of spontaneous ventricular event detected by the ventricular detection means; and
- sequencing means, adapted to define an instant of application of the stimulation after a predetermined atrioventricular delay following an atrial event detected by the atrial detection means.

In this case, according to various other advantageous subsidiary characteristics:

The ventricular detection means are means adapted to detect the occurrence, or the absence of occurrence, of a spontaneous ventricular event by analyzing the variations of the oscillating electrical signal delivered by the transducer.

The implant further includes: means for measuring the duration of the interval separating two prior consecutive spontaneous atrial and ventricular events; means for comparing the measured duration of the interval with a limit value; and means for conditionally activating the sequencing means, for the later atrial and ventricular events, when the duration exceeds the limit value.

The sequencing means are further adapted to: define the instant of application of the ventricular stimulation after a predetermined escape interval has elapsed after a prior spontaneous or stimulated ventricular event; and, after each later atrial event detected by the atrial detection means, apply a ventricular stimulation at the end of a predetermined atrioventricular delay without later ventricular event detected by the ventricular detection means, wherein the predetermined escape interval can be one among: an interval corresponding to a basis stimulation frequency; or an interval of increased duration with respect to a basis stimulation frequency.

The sequencing means are moreover adapted to temporarily activate the atrial detection means after each later spontaneous or stimulated ventricular event detected by the ventricular detection means. In this later case, the sequencing means may be adapted to activate the atrial detection means only after a predetermined blanking interval has elapsed after the detection of the later ventricular event;

The atrial detection means are moreover adapted, after each later spontaneous or stimulated ventricular event, to: upon detection of an atrial event (As), evaluate the contribution to the heartbeat of this atrial event; and decide that an atrial event is present if the evaluated contribution fulfils a predetermined criterion. In this later case, the atrial detection means may further include means adapted, beforehand, to: evaluate the contribution to the heartbeat of an atrial event in a window preceding the instant of ventricular stimulation, by a retrospective analysis of the variations of the oscillating electrical signal in the window; and determine the predetermined criterion based on the so-evaluated contribution, wherein the criterion can be one among: a threshold level reached in absolute value by the oscillating electrical signal; and/or the energy of the oscillating electrical signal over a given time interval;

The implant further includes means adapted, in case of presence of an atrial event detected by the atrial detection means and of a consecutive spontaneous or stimulated ventricular event, to calculate a mechanical atrioventricular delay counted between the respective instants of occurrence of the atrial and ventricular events; and means adapted to adjust the atrioventricular stimulation delay so as to match the value of the mechanical atrioventricular delay with a predetermined atrioventricular delay.

The atrial detection means further include means adapted, beforehand, to: evaluate the contribution to the heartbeat of an atrial event in a window preceding the instant of ventricular stimulation, by a prospective analysis of the variations of the oscillating electrical signal in the window, the window being triggered subsequently to the previous ventricular event; and determine the predetermined criterion based on the so-evaluated contribution.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

An exemplary embodiment of the device of the invention will now be described.

As regards its software aspects, the invention may be implemented by a suitable programming of the control software of a known cardiac stimulator device, for example a stimulator of the endocavitary leadless capsule type.

These devices include a programmable microprocessor or microcontroller coupled to circuits for receiving, shaping and processing electrical signals collected by electrodes arranged on the capsule, at least one of which is in contact with the myocardium, and delivering stimulation pulses to these electrodes. The adaptation of these devices to make the invention is within the reach of the one skilled in the art, and won't be described in detail. In particular, the software programs stored in memory and executed may be adapted or used to implement the functions of the invention that will be described hereinafter.

The method of the invention is indeed mainly implemented by software means, using suitable algorithms executed by a microcontroller or a digital signal processor. For the sake of clarity of the presentation, the various processings applied will be decomposed and schematized by a certain number of distinct functional modules or blocks and/or of interconnected circuits, but this representation has nevertheless only an illustrative character, these functions or circuits including common elements, corresponding in practice to a plurality of functions wholly executed by a single software.

Figure 1:
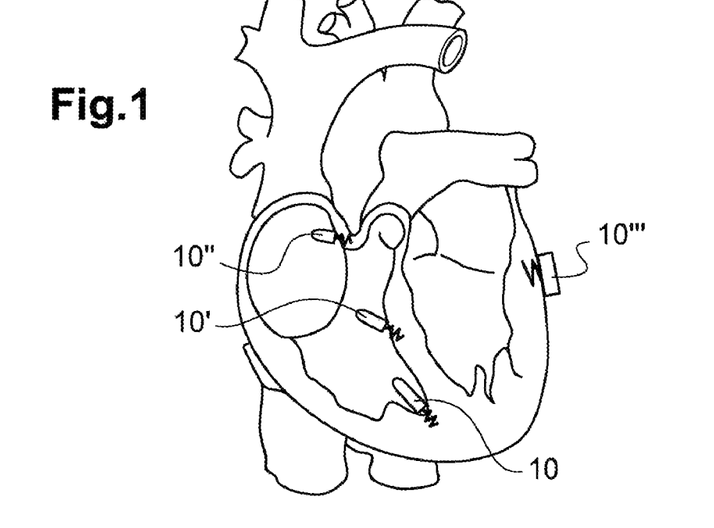
FIG. 1 illustrates a medical device of the leadless capsule type in its environment, with various examples of implantation sites in, on or near the heart of a patient.

In FIG. 1 are shown various possibilities of sites for implantation of a device of the leadless type, inside the myocardium (endocavitary implant) or on an external area of this same myocardium (epicardic implant), or also on or in a vessel close to the heart. In an advantageous preferential example, the leadless capsule 10 is implanted at the apex of the right ventricle. As a variant, the capsule may also be implanted on the right interventricular septum, as in 10', or on an outer wall of the myocardium, as in 10".

In any case, the leadless capsule is attached to the cardiac wall using a protruding anchoring system intended to enter the cardiac tissue for the holding on the implantation site. Other anchoring systems may be used and modify in no way the implementation of the present invention.

Figure 2:
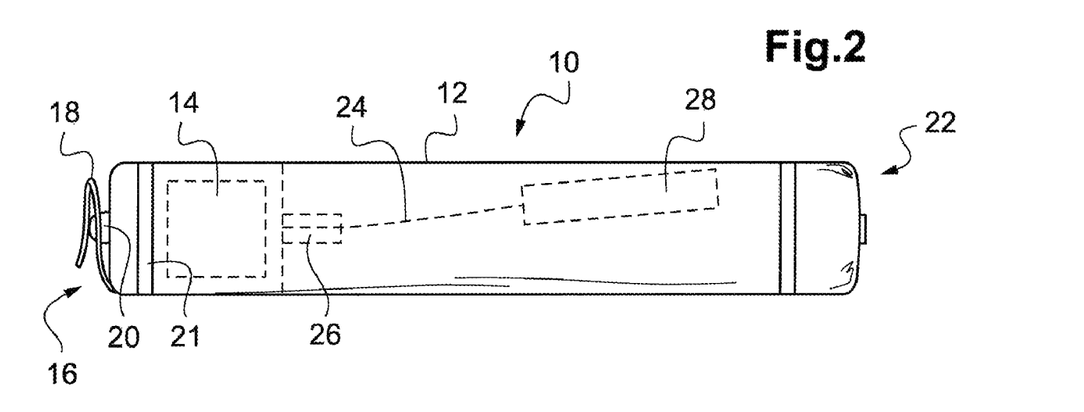
FIG. 2 is a generally longitudinal view of a leadless capsule including an energy harvester with a pendular unit.

FIG. 2 is a general longitudinal view of such a leadless capsule, including an energy harvester with a pendular unit.

The leadless capsule 10 is in this example made in the external form of a cylindrical tubular implant body 12 enclosing a unit 14 including the various electronic and power supply circuits of the capsule. The typical dimensions of such a capsule are a diameter of the order of about 6 mm over a length of about 25 mm.

At its distal end 16, the capsule carries a helical screw 18 for the anchoring of the capsule against a wall of a cardiac cavity, as illustrated hereinabove as regards FIG. 1 (this anchoring mode being of course in no way limitative). A detection/stimulation electrode 20, in contact with the cardiac tissue at the implantation site, collects the cardiac depolarization potentials and/or applies stimulation pulses. In certain embodiments, the function of the electrode 20 is provided by the anchoring screw 18, which is then an active screw, electrically conductive and connected to the detection/stimulation circuits of the capsule. The electrode 20 in contact with the tissues is generally a cathode, and is associated with an anode whose function is provided by a second remote electrode, most often an annular electrode as in 21.

The opposite proximal end 22 of the leadless capsule 10 has an atraumatic rounded shape and is provided with suitable gripping means for the connection to a guiding catheter or other implantation accessory usable at the time of positioning or explanting the capsule.

The leadless capsule 10 is provided with an energy harvesting module intended to power the electronic unit 14 and to charge an integrated energy storage component.

Such an energy harvesting module includes an inertial unit that, inside the capsule, oscillates according to the various external stresses to which the leadless capsule is subjected. These stresses may result in particular from: movements of the wall to which the capsule is anchored, which are transmitted to the implant body 12 by the anchoring screw 18; and/or blood flow variations in the environment surrounding the implant, which produce oscillations of the implant body at the heartbeat rhythm; and/or various vibrations transmitted by the cardiac tissues.

Figure 3:
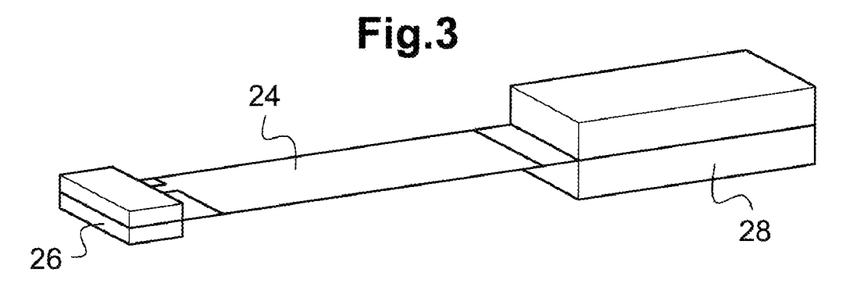
FIG. 3 shows separately the pendular unit of the leadless capsule of FIG. 2, with a piezoelectric beam coupled to an inertial mass.

FIG. 3 illustrates an example of an inertial unit for an energy harvesting module, a unit that is herein made up of a piezoelectric beam 24 fitted at one end 26 and whose opposite, free end is coupled to an inertial mass 28. The piezoelectric beam 24 is a flexible beam that, in the illustrated example, is elastically deformable according to at least one degree of freedom in longitudinal flexion.

From the mechanical point of view, this unit constitutes a pendular system of the mass-spring type (the spring being made up from the flexible piezoelectric beam) that, due to the inertia of the mass 28, oscillates as soon as the elastic beam 24 is spaced apart from its stable rest position. De facto, this unit may be likened, as regards its mechanical behavior, to a structure of the "fitted-free beam" type, which has a natural frequency of free oscillation, which is herein the frequency at which the mass-spring system oscillates.

The piezoelectric beam 24 further provides a function of mechanical-electrical transducer for converting into electrical charges the mechanical stress that is applied thereto when it is flexed, the charges being collected by electrodes formed at the surface of the beam. The beam is preferably a beam of the bimorphous type, i.e. capable of generating energy on its two faces when subjected to a deformation. These transduction properties are typical of a piezoelectric material such as the PZT ceramics or the monocrystals of the PMN-PT, barium titanate or lithium niobate type.

Of course, the invention is not limited to this particular configuration of pendular unit given as an example, and other types of inertial units may be used for the energy harvesting, such as those mentioned in introduction, from the moment that they have at least one natural frequency of free oscillation.

Likewise, the inertial unit may be a unit deformable according to several degrees of freedom, with then as much corresponding vibratory modes and natural frequencies of oscillation, and of electrical signals respectively delivered at the output.

Figure 4:
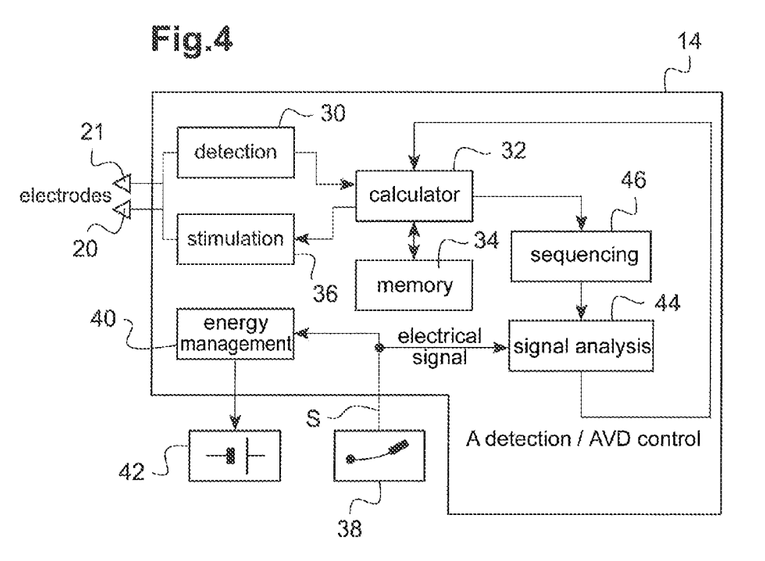
FIG. 4 shows, as a block diagram, the main internal constitutive elements of the electronic unit of the leadless capsule.

FIG. 4 is a synoptic representation of the electronic unit 14 integrated into the leadless capsule 10, shown as functional blocks. This circuit 14 is advantageously implemented as an ASIC or a combination of ASICs.

Block 30 denotes a circuit for detecting the cardiac depolarization wave, connected to the electrode 20 in contact with the cardiac tissue and to the opposite electrode 21. Block 30 includes filters and means for analog and/or digital processing of the signal collected. The so-processed signal is applied to the input of a calculator 32 associated with a memory 34.

The electronic unit 14 also includes a stimulation circuit 36 operating under the control of the calculator 32 for, as and whenever necessary, delivering myocardium stimulation pulses to the system of electrodes 20 and 21.

An energy harvesting circuit 38 is moreover provided, made up by the pendular unit formed by the piezoelectric beam 24 and the inertial mass 28 described hereinabove with reference to FIGS. 2 and 3.

This energy harvesting circuit 38 produces as an output a variable electrical signal S such as that of FIGS. 5a to 5c described hereinabove.

Firstly, the signal S is delivered to a power management circuit 40, which rectifies and regulates the signal S so as to produce as an output a stabilized direct voltage or current used for powering the electronic unit 14 and charging the energy storage component 42, which itself powers the electronic unit 14.

Secondly, this same signal S is applied to a circuit 44 for analyzing instantaneous variations of the signal in order to deliver as an output, characteristically of the invention and as will be described hereinafter, an indicator of detection (presence/absence) of an atrial contraction, as well as, as the case may be, parameters for controlling an atrioventricular delay.

The data will make it possible, as will be described hereinafter, to control, as and whenever necessary, the application of the ventricular stimulation pulses by the circuit 36.

The analysis circuit 44 operates under the control of a sequencing circuit 46 that defines the time position of one or several analysis windows determined by the calculator 32, the windows delimiting the various processings operated by the circuit 44 in order to extract from the raw signal S the desired significant information.

The circuit 44 advantageously includes a pre-processing unit, composed of analog and/or digital circuits, with a digitization system and a typically analog, digital or morphological filtering, which makes it possible to discriminate, as a function of the frequency bands, the slow waves, of atrial origin, from the faster ones, of ventricular origin.

Figure 5A:
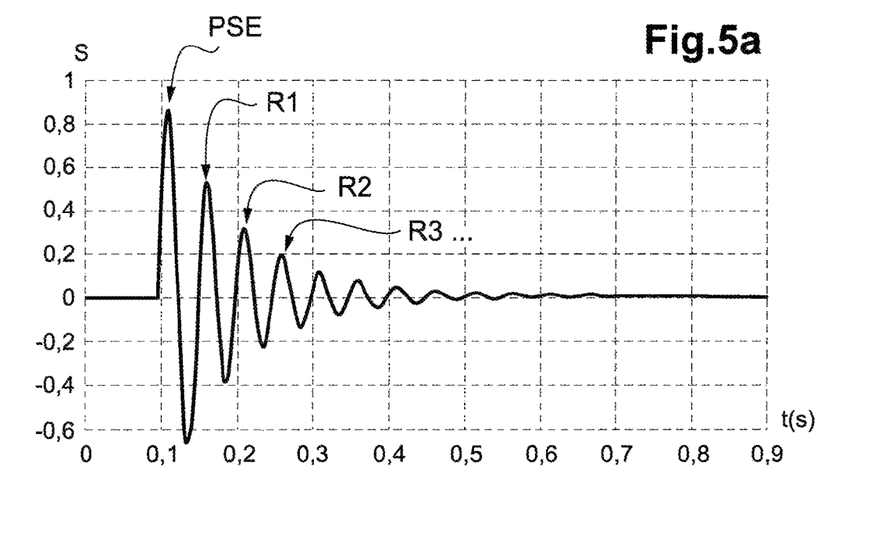
FIG. 5a is a chronogram of the oscillations of the electrical signal delivered, in an ideal situation in which the energy harvesting would have no influence on these oscillations, by the energy harvesting module of the leadless capsule after a heartbeat.
Figure 5B:
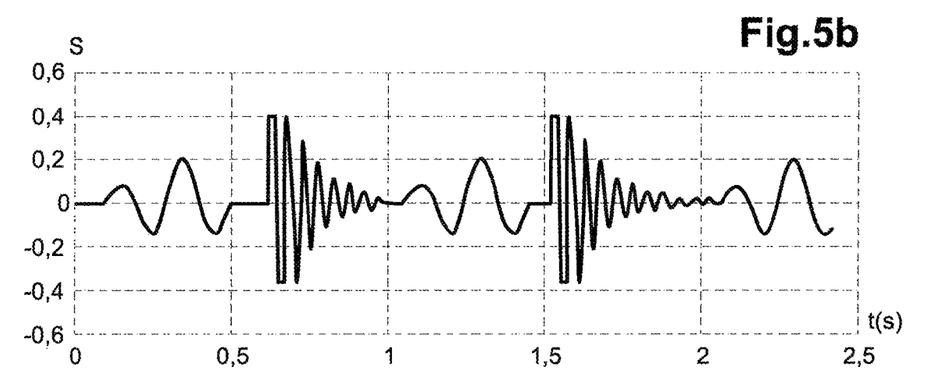
FIGS. 5b and 5c are chronograms corresponding to the oscillations illustrated in FIG. 5a, in two situations in which the energy harvesting interferes with these oscillations.
Figure 5C:
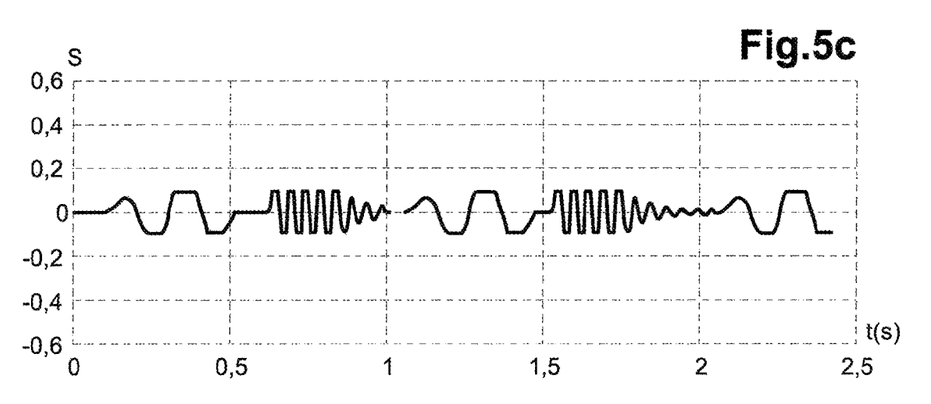

FIGS. 5a, 5b and 5c illustrate the variations of the electrical signal S delivered during a heartbeat by the energy harvester, i.e. the variable signal produced by the mechanical-electrical transducer consisted by the piezoelectric beam 24 in the illustrated example.

This signal is a recurrent signal, repeated at the rhythm of the successive heartbeats, with, at each occurrence, a series of damped sinusoidal oscillations, including a first amplitude peak PSE followed with a series of "bounces" R1, R2, R3 . . . of decreasing amplitudes. This oscillation phase is followed with a second, consecutive phase, substantially without bounce, which continues until a new contraction of the myocardium that will produce similar variations of the signal S.

The order of magnitude of the recurrence rate of the cardiac cycles is typically of 1 to 2 Hz (60 to 120 bpm (beats per minute)). The natural frequency of the pendular unit is determined by the geometry of the piezoelectric beam 24 (mainly its length and thickness), by the elasticity of the material that composes it, and by the mass of the inertial mass 28. These different parameters may be advantageously chosen so as to give the natural frequency of free oscillation a value that is far higher than that of the cardiac rhythm, for example a rate of the order of 20 Hz, this value being of course not limitative. Almost in all circumstances, the pendular unit will then produce between two heartbeats a plurality of bounces followed with a phase with no bounces before the following heartbeat.

FIG. 5a shows an ideal case in which the transducer would be charged by a pure resistance, i.e. in which the energy harvesting would have no influence on the oscillations of the electric signal delivered by the transducer.

However, concretely, the energy harvesting by the power management circuit 40 deteriorates the signal S, which is clipped as a function of a threshold value of this circuit 40.

The typical signal becomes as that illustrated in FIGS. 5b and 5c, which are chronograms corresponding to the oscillations illustrated in FIG. 5a, in two situations in which the energy harvesting interferes with these oscillations: FIG. 5b illustrates the case in which a relatively high threshold of the circuit 40 is applied, and in which only the signal S relating to the ventricular activity is clipped, whereas FIG. 5c illustrates the case in which a relatively low threshold of the circuit 40 is applied, and in which the two ventricular and atrial components of the relative signal S are clipped.

This clipping of S does not change the principle of the present invention and, for the sake of clarity of the presentation, the ideal case of FIG. 5a will be kept in mind in the following of the description, it being understood that this description may as well been applied to the case of a clipped signal S as that illustrated in FIGS. 5b and 5c.

Figure 6:
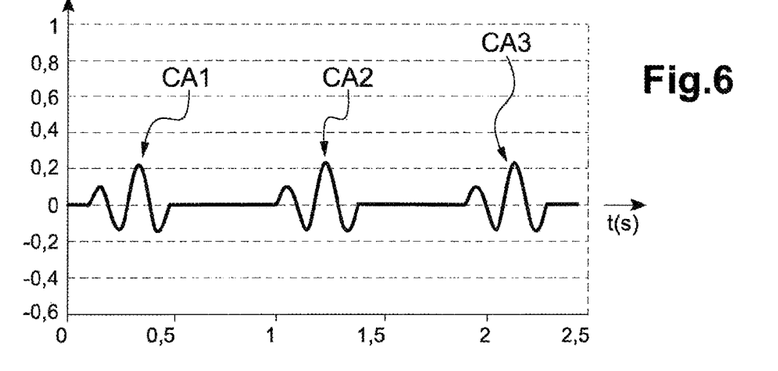
FIG. 6 illustrates separately the atrial component of the electrical signal delivered by the energy harvesting module, representative of the contribution of the atrium contraction, during three successive cardiac cycles.

FIG. 6 illustrates the variations of the electrical signal S produced by the (only) contraction of the atrium, during three successive atrial cycles CA1, CA2, CA3, with spontaneous and regular contraction of the atrium (sinoatrial rhythm). Physiologically, during the diastolic phase, the ventricles relax and fill up, and the contraction of the atriums comes in addition to this passive filling, which accelerates the phenomenon. The atrial contraction therefore produces a dilation of the ventricle walls, whose displacement is detected by the energy harvester and converted into an electrical signal S, which gives the waves CA1, CA2, CA3 representative of the atrium contribution to the movement of the ventricle walls.

Figure 7A:
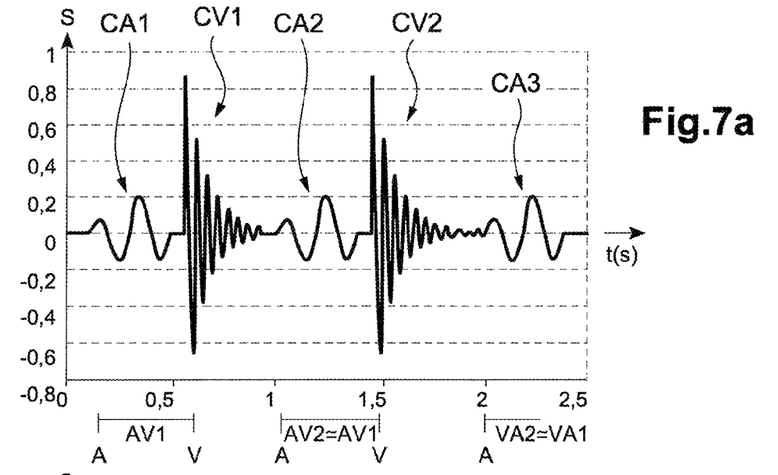
FIGS. 7a and 7b illustrate the electrical signal, delivered by the energy harvesting module, combining the atrial and ventricular components during successive heartbeats, respectively in the case of a present and non-delayed atrioventricular conduction and in the case of a partial atrioventricular block (AVB) causing a desynchronization of the atrial and ventricular rhythms.

In FIG. 7a is represented this same electrical signal S delivered by the energy harvester, during successive cardiac cycles, with the atrial components CA1, CA2 . . . (those of FIG. 6) and the ventricular components CV1, CV2 . . . that follow them at each heartbeat (and that each correspond to the type of signal illustrated and described hereinabove in relation with FIG. 5a, with a very marked signal peak followed with a succession of fast bounces).

As can be seen, the atrial contribution produces a signal CA1, CA2 . . . whose amplitude is lower, and whose frequency is lower, than those of the ventricular contribution CV1, CV2 . . . .

In FIG. 7a are also noted the atrio-ventricular intervals (or "AV delays") AV1, AV2 . . . and the ventriculo-atrial intervals (or "VA delays") VA1, VA2 . . . .

In the case, illustrated in FIG. 7a, of a normal atrioventricular conduction (absence of atrioventricular block), the two signals CA and CV are synchronous, with delays AV1, AV2 . . . varying a little from one cycle to the following one, like the delays VA1, VA2 . . . , it being understood that, in the case of the sinus variability or in case of effort, the different delays would be variable from one cycle to the other.

Figure 7B:
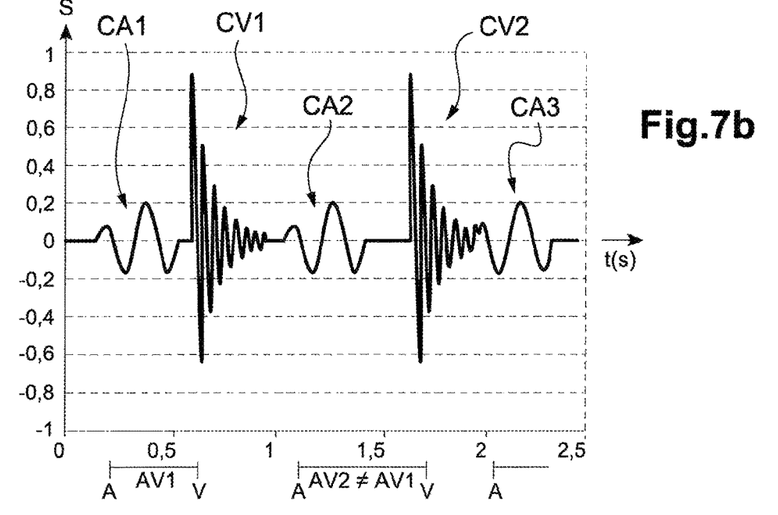

FIG. 7b is homologous to FIG. 7a, but in the presence of a partial atrioventricular block (AVB) (so-called first-degree AVB), characterized by a still present but delayed atrioventricular conduction, causing a desynchronization of the atrial and ventricular rhythms from each other.

This desynchronization produces from one cycle to the other very important variations of the AV delays. Hence, in the illustrated example, due to the AVB, the second ventricular contraction CV2 is delayed with respect to the atrial contraction CA2 of the same cycle (it will be noted that the "AV delays" are herein mechanical-mechanical delays and not electrical-electrical nor mechanical-electrical delays).

Figure 8:
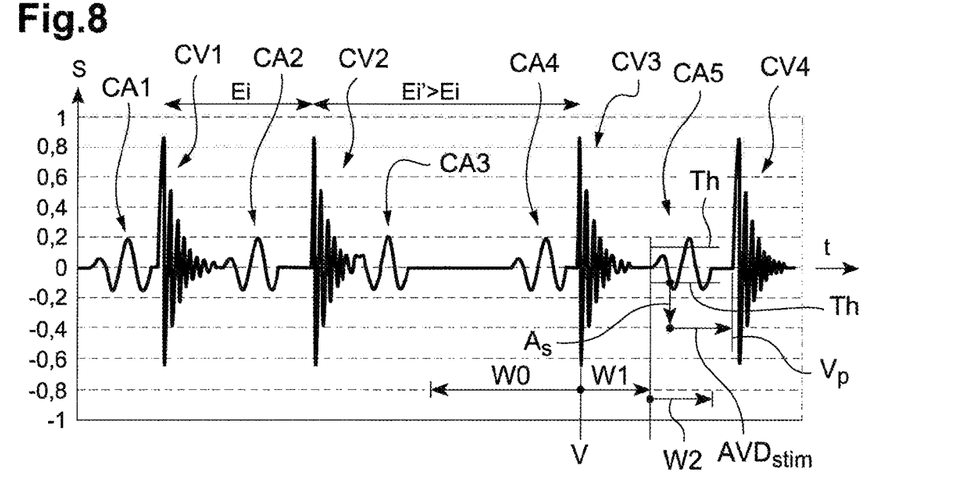
FIG. 8 illustrates the case of a complete AVB with implementation of the invention, where an elongated escape interval is applied to the search for an underlying atrial activity.

FIG. 8 illustrates the principle of the invention for detecting, by analysis of the signal S, the presence or the absence of an atrial contraction, which is necessary if it is desired to operate in VDD mode in presence of an AVB of the second degree or the third degree.

Indeed, such an AVB is characterized by the fact that a part (AVB2) or the totality (AVB3) of the atrial waves, stimulated or spontaneous, are no longer conducted, i.e. they are no longer followed with ventricular depolarizations/contractions. In such a case, the contraction of the ventricle must necessarily be triggered by a stimulation produced by the device.

In the case of a single-chamber stimulator in VVI mode, this stimulation is triggered at the end of an "escape interval" EI, which is a time interval, counted after a ventricular detection or stimulation (related to a spontaneous or stimulated contraction by an electrical pulse applied by the device), at the end of which a stimulation is delivered to the ventricle in the absence of detection of a spontaneous event of the latter.

Within the framework of the present invention, which aims at reproducing a VDD mode, the ventricular detection is made in a conventional manner, using the circuit 30 (FIG. 4) that detects a ventricular depolarization from potentials collected on the electrodes 20, 21 of the implanted capsule.

In the example illustrated in FIG. 8, the ventricular contraction CV1 of the first cardiac cycle triggers the counting of an escape interval EI at the basic rate of the stimulator, which, for a basic rate of 60 bpm, gives an escape interval EI=1000 ms after the last ventricular event. At the end of this interval EI, a stimulation is triggered, producing a consecutive ventricular contraction CV2.

The matter is then to detect the presence or the absence of an atrial contraction and, in presence of an atrial contraction, to determine the instant of occurrence of the latter, in order to:

reveal a potential situation of atrial fibrillation, typically corresponding to an absence of atrial detection characteristic of a sinus rhythm. In this case, there is no need to try to synchronize the ventricular rhythm to the atrial rhythm, because the latter is totally disordered due to the atrium fibrillation; or in the opposite hypothesis, i.e. in case of present and confirmed sinus rhythm (normal atrial activity, sinoatrial rhythm), determine the instants of occurrence of the successive atrial contractions, so as to resynchronize if necessary the ventricular stimulation to the sinus rhythm.

Advantageously, to allow a better detection of the atrial contraction, the current escape interval EI is temporarily modified by giving it an increased value EI', for example increased to 2000 ms instead of 1000 ms.

During this increased escape interval EI', the electrical signal S delivered by the energy harvester is analyzed in the following manner.

Firstly, it is advisable to exclude from the detection the detected atrial contractions that, due to a desynchronization produced by an AVB, would not be relevant to stimulate the ventricle with a regular rhythm.

Hence, in the example of FIG. 8, it may be observed, after the ventricular contraction CV2, two atrial contractions CA3 and CA4 present for the duration of the increased escape interval EI'. Among these two contractions, the contraction CA3 is not relevant because it results from a delayed contraction and is too close to the preceding ventricular contraction CV2 (this case is identical to that of contractions CV2 and CA3 in FIG. 7b). This is that contraction CA4 that it is proper to isolate, detect and analyze.

For that purpose, a detection window W0 is defined retrospectively, after the end of the increased escape interval EI' (i.e. after the ventricular stimulation V). The atrial contribution is searched for and analyzed inside this detection window W0, which, in the illustrated example, makes it possible to determine the presence of an atrial contraction CA4.

As a variant, the detection window W0, instead of being counted retrospectively after the end of the escape interval EI', may be counted prospectively, i.e. positively from the beginning of the escape interval (i.e. from the ventricular contraction CV2 in the illustrated example).

The criterion making it possible to detect the presence or the absence of an atrial contraction is for example: a threshold level reached in absolute value by the oscillating electric signal S, or the energy of this signal S (by integration of the latter over a given interval), or a combination of the preceding criteria.

The atrial detection may also include additional criteria, in particular for detecting a possible arrhythmia over several successive cycles, the atrial contraction being proved only in the absence of arrhythmia.

Once the atrial contraction detected (the contraction CA4 in the illustrated example), its variation parameters (such as maximum amplitude in absolute value, maximum amplitude excursion, root mean square value, energy, etc.) are analyzed and converted into an indicator that will be used for the later detections, for example an amplitude threshold level Th in absolute value.

For the following detection, the device opens a first window W1 for blanking the signal bounces, followed with a window W2 for atrial detection, these successive windows W1 and W2 being triggered from the instant V of the detected ventricular event (CV3 in the illustrated example).

If, in the time period of the detection window W2, the electric signal S delivered by the energy harvester fulfils the previously determined indicator (i.e., in the illustrated example, exceeds the threshold Th), then the device considers that a spontaneous atrial event As is present.

The device then begins to count an atrioventricular stimulation delay AVDstim from the instant of the spontaneous atrial contraction As that has been detected.

Figure 9:
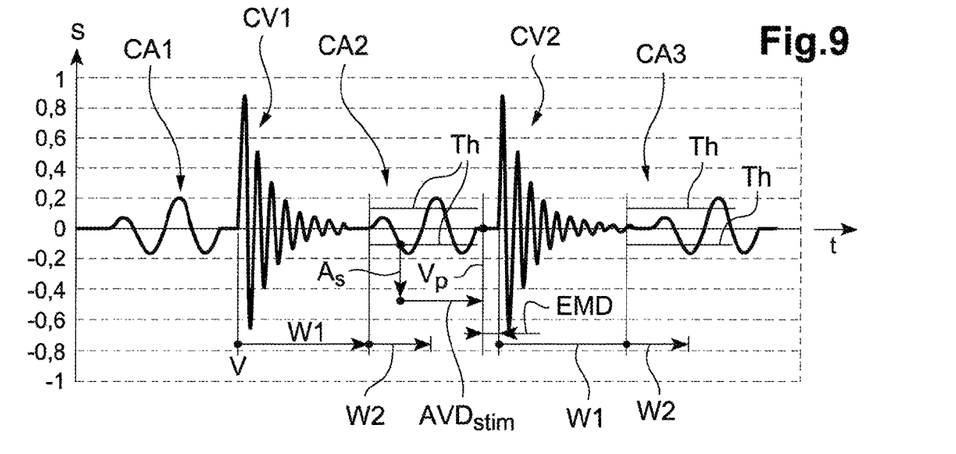
FIG. 9 illustrates the principle of implementation of the invention for the application of an atrioventricular delay to the ventricular stimulation, in the case of a present and detected atrial contraction.

This phase is more precisely illustrated in FIG. 9: if no ventricular event is detected before the end of the delay AVDstim, then a ventricular stimulation Vp is delivered by the device. This electrical stimulation produces a ventricular depolarization wave, that results in a myocardium contraction, observable on the signal S of the energy harvester as a damped oscillation, wherein this oscillation begins after a slight delay, called electromechanical delay EMD, following the ventricular stimulation Vp.

A new series of blanking W1 and detection W2 windows is then triggered, to detect the presence or the absence of a later atrial contraction (present contraction CA3 in the example illustrated in FIG. 9), as described hereinabove and using the same indicator as above (threshold indicator Th in the illustrated example).

Figure 10:
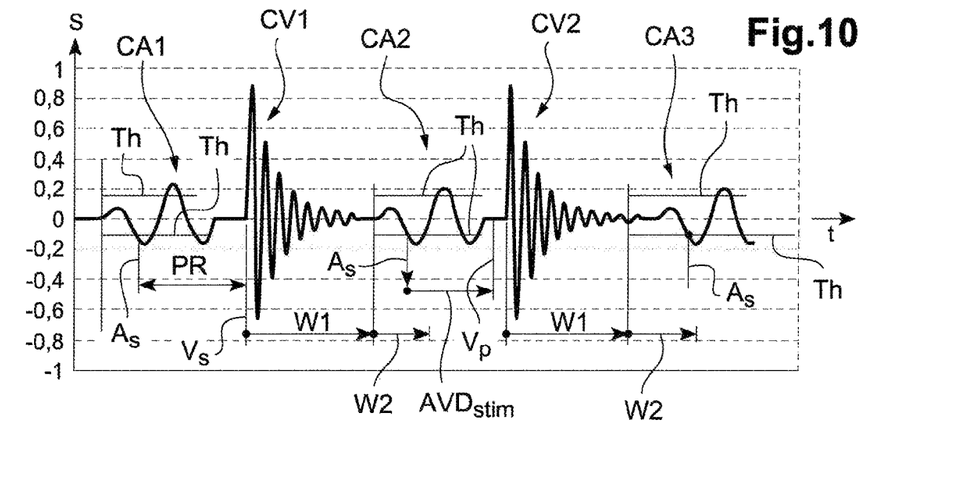
FIG. 10 is homologous to FIG. 9, in the case of a present but delayed atrioventricular conduction.

FIG. 10 is homologous to FIG. 9, in the case of a present, by delayed atrioventricular conduction (first-degree AVB).

In such a case, the just-described mechanism of the invention makes it possible to restore the synchronism between the atrial and ventricular contractions.

As illustrated in the first cycle in FIG. 10, the first-degree AVB is characterized by an excessively long atrioventricular interval PR (interval separating a spontaneous event As from a consecutive spontaneous event Vs of the ventricle).

If, at the following heartbeat, the device applies the mechanism described hereinabove in relation with FIG. 9, then, upon detection of the ventricular contraction CV1 (in this case, a spontaneous contraction Vs), a bounce blanking window W1 is triggered, followed with an atrial detection window W2.

The spontaneous atrial contraction As detected in the window W2 triggers an atrioventricular delay AVDstim producing, at the end of this delay, a ventricular stimulation Vp that allows restoring a physiological, short PR interval.

Figure 11:
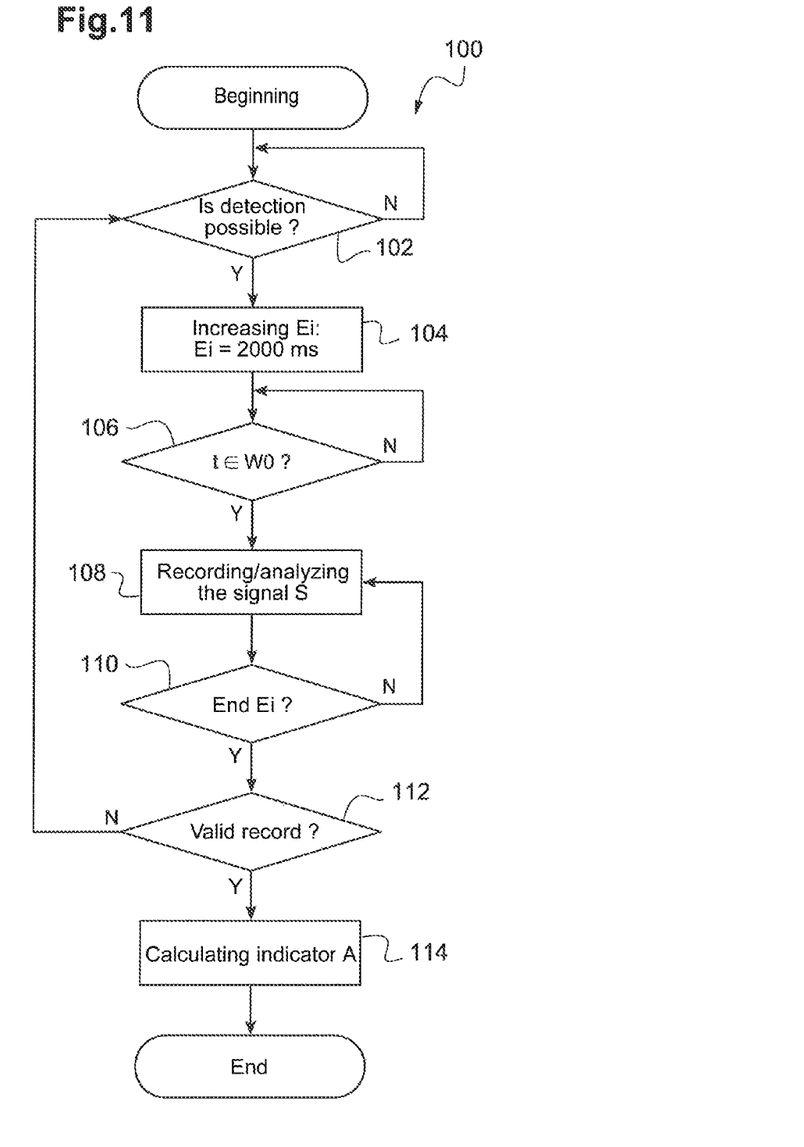
FIG. 11 is a flow diagram detailing the sequence of operations and tests for evaluating a criterion indicative of the presence or the absence of an atrial contraction, in the case of a complete AVB corresponding to the situation illustrated in FIG. 8.

FIG. 11 is a flow diagram 100 detailing the sequence of operations and tests for evaluating a criterion of presence/absence of an atrial contraction, in the case of a complete AVB (corresponding to the situation described and illustrated in FIG. 8).

The device firstly determines (test 102) whether such a detection is effectively possible, for example in the case where a prior detection has been tried but has failed; in this latter case, a waiting delay is applied before any new detection.

If the detection is possible, then the escape interval EI is increased, for example to a value EI=2000 ms (block 104).

The device then waits until the end of the detection window W0 (test 106) to begin recording, and/or analyzing on the fly, the variations of the signal S (block 108).

This action is continued up to the end of the escape interval EI (test 110), after what the device determines (test 112) whether or not the variations of the signal S, in terms of time and/or amplitude variations, correspond to an effective atrial activity. If the computing power allows it, more complex tests are possible, in particular with shape analysis of the signal S, using self-learning neuronal circuits, and/or using an artificial intelligence system.

If the result of the test 112 is negative, the process returns to the beginning of the sequence of steps, at test 102. In the opposite case, i.e. in the presence of a proven atrial event, the atrial contraction indicator is then calculated (block 114), typically as an amplitude threshold value Th in absolute value as in the example illustrated and described in FIG. 8.

Figure 12:
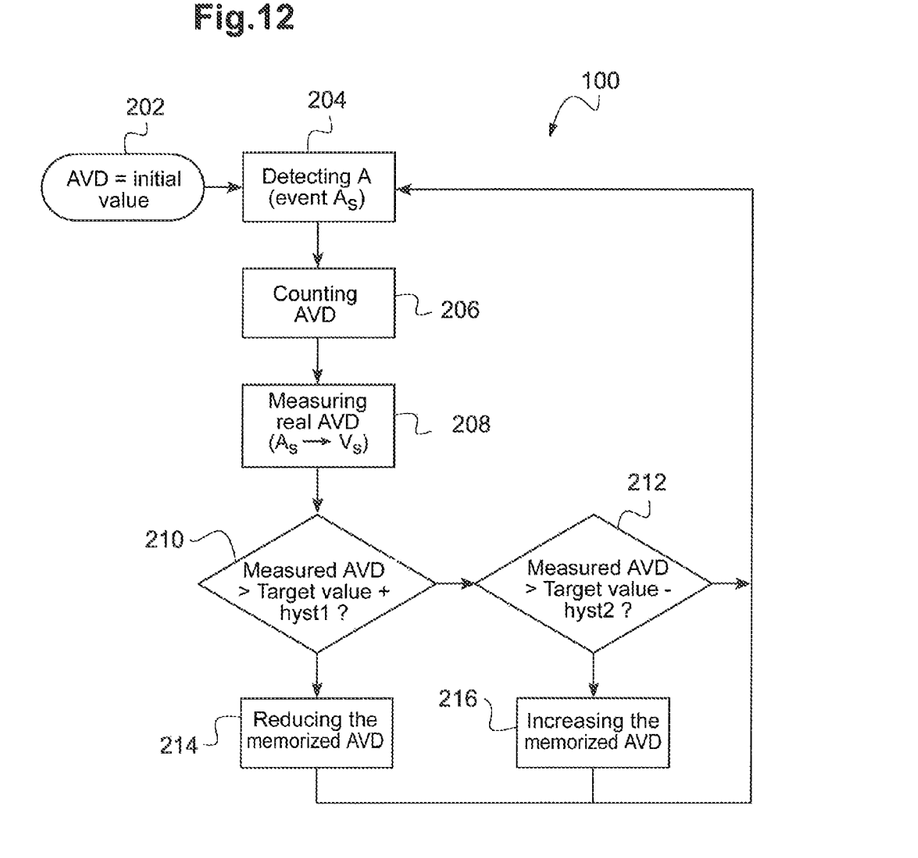
FIG. 12 is a flow diagram detailing the sequence of operations and tests for adjusting the atrioventricular delay to an optimum value from the hemodynamic point of view in the case of a present and detected atrial contraction, corresponding to the situation illustrated in FIG. 9.

FIG. 12 is a flow diagram 200 detailing the sequence of operations and tests for adjusting the atrioventricular delay to an optimum value from the hemodynamic point of view, in the case of a present and detected atrial contraction (corresponding to the situation described and illustrated in FIG. 9).

The matter is to analyze the delays between atrial and ventricular events only on the basis of components corresponding to the mechanical activity of the contractions of these cavities, so as to eliminate the effect of the electromechanical delay EMD (cf. FIG. 9) between the application of the electric ventricular stimulation pulse (at the instant Vp in FIGS. 9 and 10) and the mechanical effect produced by this pulse, i.e. the ventricle contraction itself detected by the analysis of the signal S.

The atrioventricular stimulation delay AVDstim is initially parameterized to a predetermined initial value (Block 202). Upon detection (Block 204) of an atrial contraction (at the instant As in FIGS. 8 to 10), the device begins to count an atrioventricular delay (Block 206).

If a spontaneous ventricular contraction is detected, the real atrioventricular delay (mechanical atrioventricular delay) AVDm=As−Vs is then measured (Bloc 208). This real, mechanical, atrioventricular delay AVDm is compared with a predetermined target value AVDp (tests 210, 212, with application of hysteresis limits hyst1 and hyst2).

If the measured mechanical atrioventricular delay AVDm is higher than the predetermined target value AVDp, then the memorized atrioventricular delay is reduced (Block 214). If the measured mechanical atrioventricular delay AVDm is lower than the predetermined target value AVDp, then the memorized atrioventricular delay is increased (Block 216). The so-memorized atrioventricular delay becomes the next stimulation AV delay AVDstim that will be applied after detection of an atrial activity As.

Hence, if during later cycles it is necessary to apply a stimulation (stimulated ventricular event Vp), then this stimulation will be performed with an optimized AV stimulation delay AVDstim, because corresponding to an actually measured delay in case of spontaneous event, and with no bias introduced due to the electromechanical delay EMD.

Having thus described the invention of the present application in detail and by reference to embodiments thereof, it will be apparent that modifications and variations are possible without departing from the scope of the invention defined in the appended claims as follows.

I claim:

1. An autonomous cardiac implant of a leadless capsule type, comprising an implant body provided with means for anchoring to a cardiac wall, the implant body accommodating an electronic unit and an energy harvesting module with an energy storage component for powering the electronic unit, the energy harvesting module being adapted to convert into electrical energy external stresses applied to the implant body under an effect of movements of the cardiac wall to which the implant is anchored and/or of blood flow variations in the environment surrounding the implant at a heartbeat rhythm and/or of cardiac tissue vibrations, wherein an energy harvesting module comprises:
   an inertial unit subjected to said external stresses;
   a transducer adapted to convert mechanical energy produced by oscillations of the inertial unit into an oscillating electrical signal; and
   a power management circuit, adapted to rectify and regulate said oscillating electrical signal, to deliver as an output a stabilized direct voltage or current, for powering said electronic unit and/or charging said energy storage component,
and wherein the implant further comprises atrial detection means, adapted to analyze, between successive beats, the oscillating electrical signal to derive therefrom atrial activity information proving in heartbeats the presence of an atrial event and/or to characterize an instant of occurrence thereof.

2. The implant of claim 1, wherein the atrial activity information is information about the presence/absence of an atrial contraction.

3. The implant of claim 1, further comprising:
   ventricular detection means, adapted to deliver a ventricular time marker defining an instant of occurrence of a ventricular event of a cardiac beat, and
   means for defining a detection window, preceding or following the ventricular time marker, and
   wherein the atrial detection means are means adapted to analyze variations of the oscillating electrical signal by searching for an atrial activity component within the detection window.

4. The implant of claim 3, wherein the ventricular detection means are means adapted to derive the ventricular time marker by analyzing the variations of the oscillating electrical signal delivered by the transducer.

5. The implant of claim 1, further comprising:
   ventricular detection means, adapted to detect an occurrence, or the absence of occurrence, of a spontaneous ventricular event in a heartbeat;
   ventricular stimulation means, adapted to apply a ventricular stimulation in the absence of the spontaneous ventricular event detected by the ventricular detection means; and
   sequencing means, adapted to define an instant of application of the stimulation after a predetermined atrioventricular delay following an atrial event detected by the atrial detection means.

6. The implant of claim 5, wherein the ventricular detection means are means adapted to detect the occurrence, or the absence of occurrence, of the spontaneous ventricular event by analyzing the variations of the oscillating electrical signal delivered by the transducer.

7. The implant of claim 1, further comprising:
   means for measuring a duration of the interval separating two prior consecutive spontaneous atrial and ventricular events;
   means for comparing said measured duration of the interval with a limit value; and
   means for conditionally activating sequencing means, for a later atrial and ventricular events, when said duration exceeds a limit value.

8. The implant of claim 5, wherein the sequencing means comprise:
   means adapted to define an instant of application of the ventricular stimulation after a predetermined escape interval has elapsed after a prior spontaneous or stimulated ventricular event; and
   means adapted to, after each of the later atrial events detected by the atrial detection means, apply a ventricular stimulation at an end of a predetermined atrioventricular delay without later ventricular event detected by the ventricular detection means.

9. The implant of claim 8, wherein said predetermined escape interval is one among: an interval corresponding to a basis stimulation frequency; or an interval of increased duration with respect to a basis stimulation frequency.

10. The implant of claim 5, wherein the sequencing means further comprise means adapted to temporarily activate the atrial detection means after each later spontaneous or stimulated ventricular event detected by the ventricular detection means.

11. The implant of claim 10, wherein the sequencing means further comprise means adapted to activate the atrial detection means only after a predetermined blanking interval has elapsed after the detection of the later ventricular event.

12. The implant of claim 5, wherein the atrial detection means further comprise means adapted, after each later spontaneous or stimulated ventricular event, to:
   upon detection of an atrial event, evaluate a contribution to the heartbeat of this atrial event; and
   decide that the atrial event is present if said evaluated contribution fulfils a predetermined criterion.

13. The implant of claim 12, wherein the atrial detection means further comprise means adapted, beforehand, to:
   evaluate the contribution to the heartbeat of an atrial event in a window preceding an instant of ventricular stimulation, by a retrospective analysis of the variations of the oscillating electrical signal in said window; and
   determine said predetermined criterion based on said so-evaluated contribution.

14. The implant of claim 13, wherein said criterion can be one among: a threshold level reached in absolute value by the oscillating electrical signal; and/or an energy of the oscillating electrical signal over a given time interval.

15. The implant of claim 12, wherein the atrial detection means further comprise means adapted, beforehand, to:
- evaluate the contribution to the heartbeat of an atrial event in a window preceding the instant of ventricular stimulation, by a prospective analysis of the variations of the oscillating electrical signal in said window, said window being triggered subsequently to the previous ventricular event; and
- determine said predetermined criterion based on said so-evaluated contribution.

16. The implant of claim 5, further comprising:
- means adapted, in case of the presence of the atrial event detected by the atrial detection means and of a consecutive spontaneous or stimulated ventricular event, to calculate a mechanical atrioventricular delay counted between the respective instants of occurrence of the atrial and ventricular events; and
- means adapted to adjust said atrioventricular stimulation delay so as to match the value of the mechanical atrioventricular delay with a predetermined atrioventricular delay.

* * * * *